US00H002284H

(19) United States
(12) Statutory Invention Registration
Stöhr et al.

(10) Reg. No.: US H2284 H
(43) Published: Sep. 3, 2013

(54) VACCINES FOR PROTECTING AGAINST INFLUENZA

(75) Inventors: Klaus Stöhr, Cambridge, MA (US); Philip Ralph Dormitzer, Weston, MA (US); Michael Broeker, Marburg (DE)

(73) Assignee: Novartis AG, Basel (CH)

(21) Appl. No.: 12/768,662

(22) Filed: Apr. 27, 2010

Related U.S. Application Data

(60) Provisional application No. 60/214,787, filed on Apr. 27, 2009, provisional application No. 60/216,198, filed on May 13, 2009, provisional application No. 60/238,628, filed on Aug. 31, 2009, and provisional application No. 60/279,665, filed on Oct. 22, 2009.

(51) Int. Cl.

| | |
|---|---|
| ***A61K 39/145*** | (2006.01) |
| ***A61K 39/295*** | (2006.01) |
| ***A61P 37/04*** | (2006.01) |
| ***A61P 31/16*** | (2006.01) |
| ***C12N 7/00*** | (2006.01) |
| ***C12N 5/00*** | (2006.01) |

(52) U.S. Cl. ..... 424/209.1; 424/206.1

(58) Field of Classification Search ..... 424/209.1, 424/206.1

See application file for complete search history.

(56) References Cited

U.S. PATENT DOCUMENTS

| | | | |
|---|---|---|---|
| 4,680,338 | A | 7/1987 | Sundoro |
| 4,689,338 | A | 8/1987 | Gerster |
| 4,929,624 | A | 5/1990 | Gerster et al. |
| 4,988,815 | A | 1/1991 | Andre et al. |
| 5,011,828 | A | 4/1991 | Goodman et al. |
| 5,238,944 | A | 8/1993 | Wick et al. |
| 5,266,575 | A | 11/1993 | Gerster et al. |
| 5,268,376 | A | 12/1993 | Gester |
| 5,346,905 | A | 9/1994 | Gerster |
| 5,352,784 | A | 10/1994 | Nikolaides et al. |
| 5,389,640 | A | 2/1995 | Gerster et al. |
| 5,395,937 | A | 3/1995 | Nikolaides et al. |
| 5,482,936 | A | 1/1996 | Lindstrom |
| 5,494,916 | A | 2/1996 | Lindstrom et al. |
| 5,525,612 | A | 6/1996 | Gerster |
| 5,658,731 | A | 8/1997 | Sproat et al. |
| 5,936,076 | A | 8/1999 | Higa et al. |
| 5,948,410 | A | 9/1999 | Van Scharrenburg et al. |
| 6,083,505 | A | 7/2000 | Miller et al. |
| 6,355,271 | B1 | 3/2002 | Bell et al. |
| 6,440,992 | B1 | 8/2002 | Gerster et al. |
| 6,468,544 | B1 | 10/2002 | Egorov et al. |
| 6,605,617 | B2 | 8/2003 | Renhowe et al. |
| 6,627,640 | B2 | 9/2003 | Gerster et al. |
| 6,649,372 | B1 | 11/2003 | Palese et al. |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,703,402 | B2 | 3/2004 | Gerster et al. |
| 6,743,920 | B2 | 6/2004 | Lindstrom et al. |
| 6,800,624 | B2 | 10/2004 | Crooks et al. |
| 6,809,203 | B2 | 10/2004 | Gerster et al. |
| 6,888,000 | B2 | 5/2005 | Crooks et al. |
| 6,924,271 | B2 | 8/2005 | Averett et al. |
| 6,924,293 | B2 | 8/2005 | Lindstrom |
| 2005/0070556 | A1 | 3/2005 | Averett et al. |
| 2005/0192248 | A1 | 9/2005 | Tsuji et al. |
| 2005/0215517 | A1 | 9/2005 | Rossignol et al. |
| 2010/0010199 | A1 * | 1/2010 | Tsai et al. ..... 435/235.1 |

FOREIGN PATENT DOCUMENTS

| | | | |
|---|---|---|---|
| EP | 0870508 | B1 | 10/1998 |
| EP | 1260581 | A1 | 11/2002 |
| FR | 2859633 | A1 | 3/2005 |
| WO | WO-92/15582 | A1 | 9/1992 |
| WO | WO-95/18861 | A1 | 7/1995 |
| WO | WO-96/37624 | A1 | 11/1996 |
| WO | WO-97/37000 | A1 | 10/1997 |
| WO | WO-97/37001 | A1 | 10/1997 |
| WO | WO-98/46262 | A1 | 10/1998 |
| WO | WO-99/64068 | A1 | 12/1999 |

| | | | |
|---|---|---|---|
| WO | WO-00/60050 | A2 | 10/2000 |
| WO | WO-01/04333 | A1 | 1/2001 |
| WO | WO-01/21151 | A1 | 3/2001 |
| WO | WO-01/22972 | A2 | 4/2001 |
| WO | WO-01/22992 | A2 | 4/2001 |
| WO | WO-01/64846 | A1 | 9/2001 |
| WO | WO-01/83794 | A2 | 11/2001 |
| WO | WO-01/85938 | A1 | 11/2001 |
| WO | WO-02/18383 | A2 | 3/2002 |
| WO | WO-02/28422 | A2 | 4/2002 |
| WO | WO-02/067983 | A1 | 9/2002 |
| WO | WO-02/074336 | A2 | 9/2002 |
| WO | WO-02/097072 | A1 | 12/2002 |
| WO | WO-03/011223 | A2 | 2/2003 |
| WO | WO-03/023021 | A2 | 3/2003 |
| WO | WO-03/023025 | A1 | 3/2003 |
| WO | WO-03/043415 | A1 | 5/2003 |
| WO | WO-03/076601 | A1 | 9/2003 |
| WO | WO-03/082272 | A1 | 10/2003 |
| WO | WO-03/105769 | A2 | 12/2003 |
| WO | WO-2004/018455 | A1 | 3/2004 |
| WO | WO-2004/060308 | A2 | 7/2004 |
| WO | WO-2004/064715 | A2 | 8/2004 |
| WO | WO-2004/064759 | A2 | 8/2004 |
| WO | WO-2004/087153 | A2 | 10/2004 |
| WO | WO-2005/042728 | A2 | 5/2005 |
| WO | WO-2005/102049 | A1 | 11/2005 |
| WO | WO-2005/113756 | A1 | 12/2005 |
| WO | WO-2005/113758 | A1 | 12/2005 |
| WO | WO-2006/027698 | A1 | 3/2006 |
| WO | WO-2006/067211 | A1 | 6/2006 |
| WO | WO-2006/071563 | A2 | 7/2006 |
| WO | WO-2006/108846 | A1 | 10/2006 |
| WO | WO-2007/002008 | A2 | 1/2007 |
| WO | WO-2007/052163 | A2 | 5/2007 |

OTHER PUBLICATIONS

Chen et al. Virol. 2006, vol. 345, No. 2, pp. 416–423.*
Snyder et al. J. Virol. 1988, vol. 62, No. 2, pp. 488–495.*
Massab et al. Rev Med Virol. 1999 Oct.–Dec.;9 (4):237–244.*
Andrianov et al. 91998) *Biomaterials* 19:109–115.
Banzhoff (2000) *Immunology Letters* 71:91–96.
Beignon et al. (2002) *Infect Immun* 70: 3012–3019.
Brands et al. (1999) *Dev Biol Stand* 98:93–100.
Briggs (1991) *J Parenter Sci Technol.* 45:7–12.
Bright et al. (2008) *PLoS ONE* 3:e1501.
Bruhl et al. (2000) *Vaccine* 19:1149–58.
Caillet et al. (2010) *Vaccine* 28:3076–3079.
Centers for Diseases Control and Prevention. (May 22, 2009) *MMWR* 58(19):521–56.
Chen et al. (2003) *Vaccine* 21:2830–2836.
Clark et al. (2009) *NEJM* 361:2424–35.
Cooper (1995) *Pharm Biotechnol* 6:559–80.
Couceiro & Baum (1994) *Mem Inst Oswaldo Cruz* 89(4):587–91.
Crevar & Ross (2008) *Virology Journal* 5(131), 9 pages.
de Jong et al. (2003) *Dev. Biol* (*Basel*) 115:63–73.
De Libero et al. (2005) *Nature Reviews Immunology* 5:485–496.
Del Giudice et al. (2009) *Sci Transl Med.* 1(12):1–3.
Dolin et al. (1977) *J Infect. Dis.* 136(Suppl.):S435–S442.
Doroshenko & Halperin (2009) *Expert Rev Vaccines* 8:679–88.
Dyakonova et al. (2004) *Int Immunopharmacol* 4(13):1615–23.
Efferson et al. (2006) *J Viral.* 80(1):383–94.
Ershler et al. (2007) *Ann N Y Acad Sci.* 1112:375–84.
Evans et al. (2003) *Expert Rev Vaccines* 2:219–229.
Galli et al. (2009) *PNAS USA* 106:7962–7.
Gambaryan & Matrosovich (1992) *J Virol Methods* 39(1–2):111–23.
Garten et al. (2009) *Science* 325:197–201.
GenBank sequence GI:325176, (Aug. 2, 1993), 1 page.
GenBank sequence GI:325237, (Aug. 2, 1993), 1 page.
Gennaro (2000) *Remington: The Science and Practice of Pharmacy.* 20th edition, ISBN: 0683306472.
Goff et al (2004) *J Am. Chem. Soc.* 126:13602–13603.
Greenbaum et at. (2004) *Vaccine* 22:2566–2577.
Greenberg et al. (2009) *NEJM* 361(25):2405–2413.
*Guidance for Industry: Bioanalytical Method Validation,* (May 2001). U.S. Department of Health and Human Services Food and Drug Administration Center for Drug Evaluation and Research (CDER) Center for Veterinary Medicine (CVM).
Halperin et al. (2002) *Vaccine* 20:1240–7.
Halperin et al. (1979) *Am J Public Health* 69:1247–1250.
Hehme et al. (2004) *Virus Res.* 103(1–2):163–171.
Herbert et al. (1979) *J Infect Dis* 140:234–238.
Herlocher et al. (2004) *J Infect Dis* 190(9):1627–30.
Hoffmann et al. (2002) *Vaccine* 20:3165–3170.
Hoffmann et al. (2000) *Virology* 267(2):310–7.
Huckriede et al. (2003) *Methods Enzymol* 373:74–91.
Hussain et al. (2010) *Vaccine* 28(22):3848–3855.
Ji et al. (2002) *Biotechniques* 32:1162–7.
Jin et al. (2003) *Virology* 306:18–24.
Johnson et al. (1999) *Bioorg Med Chem Lett* 9:2273–2278.
Jones (2003) *Curr Opin Invest Drugs* 4:214–218.
Keitel et al. (1996) *Clin Diagn Lab Immunol* 3:507–10.
Kistner et al. (1998) *Vaccine* 16:960–8.
Kistner et al. (1999) *Dev Biol Stand* 98:101–10.
Kistner et al. (2010) *PLoS ONE* 5(2): e9349.
Kitikoon et al. (2010) *Vaccine* 28:523–31.
Lahijani et al. (1998) *Hum Gene Ther.* 9:1173–80.
Liu et al. (2003) *Virology* 314:580–90.
Lokteff et al. (2001) *Biologicals* 29:123–32.
Lundblad (2001) *Biotechnology and Applied Biochemistry* 34:195–7.
Mann et al. (2004) *Vaccine* 22:2425–9.
Mastrosovich et al. (1999) *J Virol* 73:1146–55.
McCullers et al. (1999) *J Virol* 73:7343–8.
Meraldi et al. (2003) *Vaccine* 21:2485–2491.
Munster et al. (2009) *Science* 325:481–3.
Neumann et al. (2005) *Proc Natl Acad Sci USA* 102:16825–29.
Nony et al. (2001) *Vaccine* 27:3645–51.
Oki et al. (2004) *J Clin. Investig.* 113:1631–1640.
Ozaki et al. (2004) *J. Virol.* 78:1851–7.
Pajak et al. (2003) *Vaccine* 21:836–842.
Partidos et al. (1999) *Immunol Lett* 67:209–216.
Pau et al. (2001) *Vaccine* 19:2716–21.
Payne et al. (1998) *Adv Drug Delivery Review* 31:185–196.
Peppeloni et al. (2003) *Expert Rev Vaccines* 2:285–293.
Piascik (2003) *J am Pharm Assoc* (*Wash DC*). 43:728–30.
Pine et al. (2002) *J Control Release* 85:263–270.
Pizza et al. (2000) *Int J Med Microbiol* 290:455–461.
Pizza et al. (2001) *Vaccine* 19:2534–2541.
Poole & Mussett (1989) *J Biol Stand* 17:161–71.
Poole et al. (1997) *J Endotoxin* Res 4:221–31.
Potter & Oxford (1979) *Br Med Bull* 35:69–75.
Quan et al. (2010) *PLoS ONE* 5(2):e9161.

Roman et al. (2010) *Vaccine* 28:1740–45.
Ryan et al. (1999) *Infect Immun* 67:6270–6280.
Scharton–Kersten et al. (2000) *Infect Immun* 68:5306–5313.
Schellack et al. (2006) *Vaccine* 24:5461–72.
Signorelli & Hadden (2003) *Int Immunopharmacol* 3(8):1177–86.
Smith et al. (2009) *Nature* 459:1122–5.
Stanley (2002) *Clin Exp Dermatol* 27:571–577.
Stephenson et al. (2003) *Vaccine* 21:1687–93.
Stevens et al. (2006) *J Mol Biol* 355:1143–55.
Subbarao et al. (2003) *Virology* 305:192–200.
Talbot et al. (2008) *Vaccine* 26:4057–61.
Tebbey et al. (2000) *Vaccine* 18:2723–34.
Treanor et al. (1996) *J Infect Dis* 173:1467–70.
Tree et al. (2001) *Vaccine* 19:3444–50.
Powell & Newman, eds., (1995). *Vaccine Design: The Subunit and Adjuvant Approach* Plenum Press (ISBN 0–306–44867–XP).
Plotkin & Orenstein, eds., (2004) *Vaccines.* 4th edition, ISBN: 0–7216–9688–0.
Vajo et al. (2010) *Lancet* 375:49–55.
Vasilakos et al. (2000) *Cell Immunol.* 204(1):64–74.
Webby et al. (2004) *Lancet* 363:1099–103.
Wong et al. (2003) *J Clin Pharmacol* 43(7):735–42.
Wu et al. (2004) *Antiviral Res.* 64(2):79–83.
Yang et al. (2004) *Angew. Chem. Int. Ed.* 43:3818–3822.
Zangwill et al. (2008) *J Infect Dis.* 197(4):580–3.
Zurbriggen et al. (2003) *Expert Rev Vaccines* 2:295–304.

* cited by examiner

*Primary Examiner*—Daniel Pihulic
(74) *Attorney, Agent, or Firm*—Morrison & Foerster LLP

(57) ABSTRACT

A live attenuated influenza vaccine contains a H1 subtype influenza A strain. Its hemagglutinin is more closely related to SEQ ID NO: 1 than to SEQ ID NO: 3.

2 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

FIGURE 1
FIGURE 1A
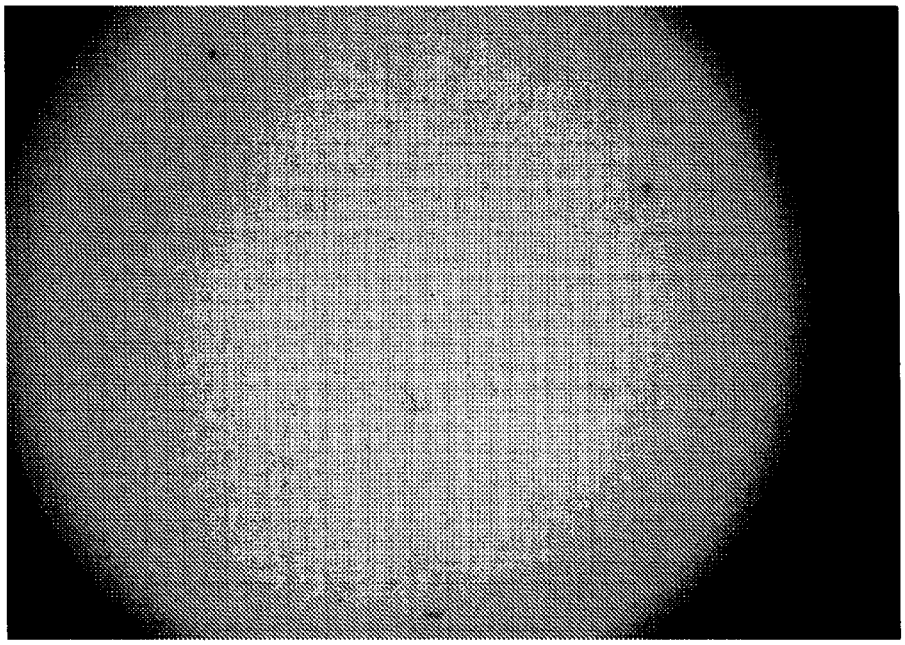
FIGURE 1B
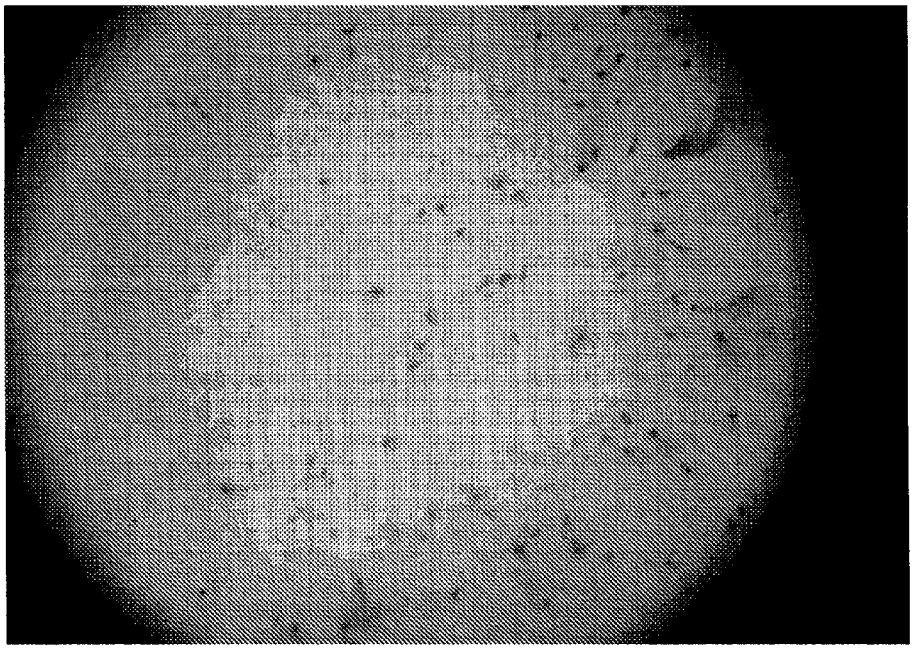

VACCINES FOR PROTECTING AGAINST INFLUENZA

This application claims the benefit of U.S. provisional applications 61/214,787 filed Apr. 27, 2009, 61/216,198 filed May 13, 2009, 61/238,628 filed Aug. 31, 2009, and 61/279,665 filed Oct. 22, 2009. No subject matter of these provisional applications has been inadvertently omitted from the present application.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002113100SEQLIST.txt, date recorded: Apr. 27, 2010, size: 51 KB).

TECHNICAL FIELD

This invention is in the field of live attenuated vaccines for protecting against influenza virus infection, and in particular against the swine flu strain(s) which emerged in April 2009. The invention described and claimed herein is not concerned with any influenza vaccines except for live attenuated influenza vaccines.

BACKGROUND ART

In April 2009 a human outbreak of swine flu was confirmed in many countries including Mexico and USA, and then spread rapidly across the globe. A pandemic was declared by the WHO in June 2009. The disease was caused by a newly identified swine influenza virus A/California/04/2009 A(H1N1). This swine flu strain seems to have no immunological cross-reactivity with current human influenza vaccines strains, including the A(H1N1) antigens in current human seasonal vaccines. The virus has been referred to variously as 'swine influenza', 'novel swine-origin H1N1 influenza', 'human-swine influenza', 'novel influenza A(H1N1)' and 'influenza A(H1N1)v'.

There is a need for a vaccine to prevent further human-to-human transmission of this swine flu and variants of it.

SUMMARY OF THE DISCLOSURE

The invention provides a live attenuated influenza vaccine, wherein the virus in the vaccine has a hemagglutinin genome segment which encodes a H1 hemagglutinin which is more closely related to SEQ ID NO: 1 than to SEQ ID NO: 3.

The invention also provides a process for preparing a vaccine, comprising growing an attenuated influenza virus in eggs, harvesting the virus, diluting the harvested virus, and formulating the diluted virus as a live attenuated influenza virus vaccine for intranasal administration, wherein the attenuated influenza virus has a hemagglutinin genome segment which encodes a H1 hemagglutinin which is more closely related to SEQ ID NO: 1 than to SEQ ID NO: 3.

The invention also provides a process for preparing a vaccine, comprising growing an attenuated influenza virus in MDCK cells, harvesting the virus, diluting the harvested virus, and formulating the diluted virus as a live attenuated influenza virus vaccine for intranasal administration, wherein the attenuated influenza virus has a hemagglutinin genome segment which encodes a H1 hemagglutinin which is more closely related to SEQ ID NO: 1 than to SEQ ID NO: 3.

The vaccine strain's neuraminidase genome segment may encode a neuraminidase which is more closely related to SEQ ID NO: 4 than to SEQ ID NO: 5.

The invention also provides a process for preparing a live attenuated influenza vaccine comprising steps of: (i) growing an influenza virus with a viral hemagglutinin gene segment encoding a hemagglutinin which is more closely related to SEQ ID NO: 1 than to SEQ ID NO: 3 and with at least one other viral segment from the AA/6/60 influenza virus strain; and (ii) formulating virus grown in step (i) as the vaccine. The viruses may be grown in eggs in step (i). Step (ii) may involve: filtering harvested allantoic fluid from eggs; concentration by ultracentrifugation; addition of stabilizing buffer to the concentrated virus; sterile filtration; and dilution to a desired potency e.g. to between $10^{6.5}$ and $10^{7.5}$ FFU (fluorescent focus units) of live attenuated virus per dose. The vaccine produced by this process may include monosodium glutamate (e.g. at a final concentration 0.09% w/v), hydrolyzed porcine gelatin (e.g. at a final concentration 1.00% w/v), arginine (e.g. at a final concentration 1.21% w/v), sucrose (e.g. at a final concentration 6.84% w/v) and/or phosphate (e.g. at a final concentration 1.61% w/v). The formulated vaccine can then be filled directly into individual sprayers for nasal administration.

The invention also provides an influenza A virus, wherein (a) the viral hemagglutinin gene encodes a hemagglutinin which is more closely related to SEQ ID NO: 1 than to SEQ ID NO: 3 and (b) at least one other viral gene is from the AA/6/60 (A/Ann Arbor/6/60) influenza virus strain. These reassortant strains are useful for preparing live attenuated vaccines.

The invention also provides an influenza A virus, wherein (a) the viral hemagglutinin gene encodes a hemagglutinin protein which has at least k % sequence identity to SEQ ID NO: 1, where k is 85 or more e.g. 85, 88, 90, 92, 94, 95, 96, 97, 98, 99 or more (e.g. 100), and (b) at least one other viral gene is from the AA/6/60 influenza virus strain (A/Ann Arbor/6/60). These reassortant strains are useful for preparing live attenuated vaccines.

BRIEF DESCRIPTION OF THE DRAWINGS

FIG. 1 shows the results of a reverse genetics experiment.

DETAILED DESCRIPTION OF EMBODIMENTS

Vaccine strains

Figure 2:
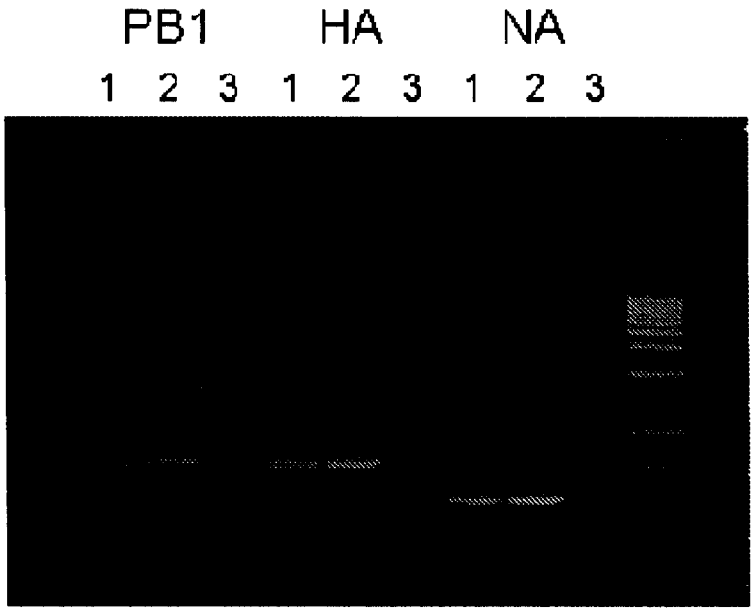
FIG. 2 shows the results of PCR amplification from rescued virus.

The invention uses a live attenuated influenza A virus strain as a vaccine antigen. The strain in the vaccine encodes a hemagglutinin antigen which, when (if) administered to a human subject in polypeptide form (e.g. unadjuvanted), elicits anti-hemagglutinin antibodies which cross-react with A/California/04/2009 hemagglutinin (SEQ ID NO: 1; GI:227809830). In other embodiments the hemagglutinin is from A/Califomia/04/2009 (SEQ ID NO: 1). In other embodiments the hemagglutinin comprises an HA1 amino acid sequence having at least i % sequence identity to SEQ ID NO: 2, where i is 85 or more e.g. 85, 88, 90, 92, 94, 95, 96, 97, 98, 99 or more.

H1N1 strains which encode suitable HA antigens include A/California/04/2009 itself, A/California/7/2009, A/Texas/5/2009, A/England/195/2009, and A/New York/18/2009.

The hemagglutinin is more closely related to SEQ ID NO: 1 (A/California/04/2009) than to SEQ ID NO: 3 (A/Chile/1/1983). A hemagglutinin which is more closely related to SEQ ID NO: 1 than to SEQ ID NO: 3 (i.e. has a higher degree sequence identity when compared to SEQ ID NO: 1 than to SEQ ID NO: 3 using the same algorithm and parameters) is referred to hereafter as a 'H1*' hemagglutinin. SEQ ID NOs: 1 and 3 are 80.4% identical.

Useful full-length H1 hemagglutinin sequences for use with the invention include SEQ ID NO: 1, SEQ ID NO: 6, SEQ ID NO: 7, SEQ ID NO: 9, SEQ ID NO: 11, as well as those comprising an amino acid sequence having at least i % sequence identity to SEQ ID NO: 2 as discussed above, or having at least i % sequence identity to SEQ ID NO: 12. Ideally the hemagglutinin does not include a hyper-basic regions around the HA1/HA2 cleavage site. Preferred hemagglutinins have a binding preference for oligosaccharides with a Sia(α2,6)Gal terminal disaccharide compared to oligosaccharides with a Sia(α2,3)Gal terminal disaccharide (see below).

SEQ ID NO: 11 (comprising SEQ ID NO: 12) is a useful H1* hemagglutinin. It differs from SEQ ID NO: 1 at residues 214, 226 and 240 (i.e. 99.47% identity).

The vaccine strain may be a reassortant e.g. it may include one or more non-HA and non-NA genome segments ("backbone segments") from, for instance, an A/Ann Arbor/6/60 strain. Thus the virus may include at least one of segments NP, M, NS, PA, PB1 and/or PB2 from AA/6/60. The encoded PB1 protein may include one or more of K391E, E581G &/or A661T mutations in PB1, a N265S mutation in PB2, and/or a D34G mutation in NP.

The vaccine strain may be a cold-adapted ("ca") strain i.e. it can replicate efficiently at 25° C., a temperature that is restrictive for replication of many wildtype influenza viruses. The strain may be temperature-sensitive ("ts") i.e. its replication is restricted at temperatures at which many wild-type influenza viruses grow efficiently (37-39° C.). The strain may be attenuated ("att") e.g. so as not to produce influenza-like illness in a ferret model of human influenza infection. The cumulative effect of the antigenic properties and the ca, ts, and att phenotype is that the virus in the attenuated vaccine can replicate in the nasopharynx to induce protective immunity in a typical human patient but does not cause disease i.e. it is safe for general administration to the target human population. A live attenuated vaccine of the invention may be tested (e.g. at the bulk stage or at the individual dose stage) for one or more (preferably all) of the ca, ts and att phenotypes.

The influenza virus strain maybe resistant to antiviral therapy (e.g. resistant to oseltamivir [1] and/or zanamivir).

In some embodiments, strains used with the invention will thus have hemagglutinin with a binding preference for oligosaccharides with a Sia(α2,6)Gal terminal disaccharide compared to oligosaceharides with a Sia(α2,3)Gal terminal disaccharide. Human influenza viruses bind to receptor oligosaccharides having a Sia(α2,6)Gal terminal disaccharide (sialic acid linked α-2,6 to galactose), but eggs and Vero cells have receptor oligosaccharides with a Sia(α2,3)Gal terminal disaccharide. Growth of human influenza viruses in cells such as MDCK provides selection pressure on hemagglutinin to maintain the native Sia(α2,6)Gal binding, unlike egg passaging. To determine if a virus has a binding preference for oligosaccharides with a Sia(α2,6)Gal terminal disaccharide compared to oligosaccharides with a Sia(α2,3)Gal terminal disaccharide, various assays can be used. For instance, reference 2 describes a solid-phase enzyme-linked assay for influenza virus receptor-binding activity which gives sensitive and quantitative measurements of affinity constants. Reference 3 used a solid-phase assay in which binding of viruses to two different sialylglycoproteins was assessed (ovomucoid, with Sia(α2,3)Gal determinants; and pig $\alpha_2$-macroglobulin, which Sia(α2,6)Gal determinants), and also describes an assay in which the binding of virus was assessed against two receptor analogs: free sialic acid (Neu5Ac) and 3'-sialyllactosc (Neu5Acα2-3Galβ1-4Glc). Reference 4 reports an assay using a glycan array which was able to clearly differentiate receptor preferences for α2,3 or α2,6 linkages. Reference 5 reports an assay based on agglutination of human erythrocytes enzymatically modified to contain either Sia(α2,6)Gal or Sia(α2,3)Gal. Depending on the type of assay, it may be performed directly with the virus itself, or can be performed indirectly with hemagglutinin purified from the virus.

In some embodiments the H1 hemagglutinin has a different glycosylation pattern from the patterns seen in egg-derived viruses. Thus the HA (and other glycoproteins) in the virus may include glycoforms that are not seen in chicken eggs. Useful HA includes canine glycoforms.

The live attenuated virus also encodes a neuraminidase protein. The strain may express one or more of influenza A virus NA subtypes N1, N2, N3, N4, N5, N6, N7, N8 or N9, but it will usually be a N1 strain (e.g. a H1N1 virus) or N2 (e.g. a H1N2 virus). The neuraminidase may have at least j % sequence identity to SEQ ID NO: 4, where j is 75 or more e.g. 75, 80, 85, 88, 90, 92, 94, 95, 96, 97, 98, 99 or more (e.g. 100). Many such sequences are available. In some embodiments, the neuraminidase is more closely related to SEQ ID NO: 4 than to SEQ ID NO: 5. SEQ ID NOs: 4 and 5 are 82% identical.

A live attenuated influenza A virus strain can have a genome encoding a hemagglutinin with amino acid sequence SEQ ID NO: 6. Compared to SEQ ID NO: 1 this sequence has Pro-200 instead of Ser-200. This hemagglutinin may include a HA1 sequence with at least 90% (e.g ≧91%, ≧92%, ≧93%, ≧94%, ≧95%, ≧96%, ≧97%, ≧98%, ≧99%) identity to SEQ ID NO: 2, provided that it includes the Pro-200 residue.

A live attenuated influenza A virus strain can have a genome encoding a hemagglutinin with amino acid sequence SEQ ID NO: 7 or comprising SEQ ID NO: 8. Compared to SEQ ID NO: 1 this sequence has Glu-204 instead of Asp-204 and has a deletion of Lys-147.

A live attenuated influenza A virus strain can have a genome encoding a hemagglutinin with amino acid sequence SEQ ID NO: 9 or comprising SEQ ID NO: 10. Compared to SEQ ID NO: 7 this sequence has Ser-159 instead of Lys-159, Ser-206 instead of Gln-206, Ala-241 instead of Glu-241, and Glu-170 instead of Lys-170.

A live attenuated influenza A virus strain can have a genome encoding a hemagglutinin with amino acid sequence SEQ ID NO: 13. Compared to SEQ ID NO: 1 this sequence has Ile-208 instead of Leu-208. This hemagglutinin may include a HA1 sequence with at least 90% (e.g ≧91%, ≧92%, ≧93%, ≧94%, ≧95%, ≧96%, ≧97%, ≧98%, ≧99%) identity to SEQ ID NO: 2, provided that it includes the Ile-208 residue.

A live attenuated influenza A virus strain can have a genome encoding a hemagglutinin which is more closely related to SEQ ID NO: 1 than to SEQ ID NO: 3, and which has one or more of (i) a proline residue at the position corresponding to Ser-200 in SEQ ID NO: 1, (ii) a glutamate residue at the position corresponding to Asp-204 in SEQ ID NO: 1, (iii) a serine residue at the position corresponding to Lys-159 in SEQ ID NO: 1, (iv) a serine residue at the position corresponding to Gln-206 in SEQ ID NO: 1, (v) an alanine residue at the position corresponding to Glu-241 in SEQ ID NO: 1, (vi) a glutamate residue at the position corresponding to Lys-170 in SEQ ID NO: 1, (vii) an isoleucine residue at the position corresponding to Leu-208 in SEQ ID NO: 1, and/or (viii) an aspartate residue at the position corresponding to Asn-173 in SEQ ID NO: 1.

Additional strains

A live attenuated influenza vaccine of the invention may be a monovalent vaccine (i.e. it includes a single live attenuated influenza virus strain) or it may include at least two (e.g. 2, 3, 4, or more) different live attenuated strains. In a multivalent live attenuated vaccine of the invention, at least one of the strains has a hemagglutinin genome segment which encodes a H1 hemagglutinin which is more closely related to SEQ ID NO: 1 than to SEQ ID NO: 3.

A process of the invention can include steps of separately growing different attenuated influenza virus strains, harvesting the different viruses, diluting the different harvested viruses, and formulating the different diluted viruses as a multivalent live attenuated influenza virus vaccine for intranasal administration. One of the strains has a hemagglutinin genome segment which encodes a H1 hemagglutinin which is more closely related to SEQ ID NO: 1 than to SEQ ID NO: 3.

In addition to including a live attenuated H1* strain, compositions of the invention may include one or more (e.g. 1, 2, 3, 4 or more) additional live attenuated influenza virus strains, which may be influenza A and/or influenza B virus strain(s). Thus a composition may include one or more strains with HA characteristic of a normal seasonal vaccine plus at least one H1* strain e.g. a 4-valent vaccine with two H1 strains (one strain with a H1* hemagglutinin, one H1 strain with a non-H1* hemagglutinin), a H3N2 strain, and one influenza B strain, or a 5-valent vaccine with two H1 strains (one a H1* strain, one not a H1* strain), a H3N2 strain, and two influenza B virus strains (a B/Victoria/2/87-like strain and a B/Yamagata/16/88-like strain).

The invention also provides a 2-valent vaccine comprising a live attenuated H1* strain and a live attenuated H5 strain.

The invention also provides a trivalent vaccine comprising a live attenuated H1* strain, a live attenuated H3N2 influenza A virus strain and a live attenuated influenza B virus strain.

The invention also provides an immunogenic composition comprising two different live attenuated H1 influenza A virus strains, wherein (i) the first H1 subtype influenza A virus strain encodes a hemagglutinin which is more closely related to SEQ ID NO: 1 than to SEQ ID NO: 3 and (ii) the second H1 subtype influenza A virus strain encodes a hemagglutinin which is more closely related to SEQ ID NO: 3 than to SEQ ID NO: 1. This mixture of H1 hemagglutinins offers a broader spectrum of protection against H1 influenza A virus strains than currently available. This composition may also include (iii) a H3N2 and/or (iv) an influenza B live attenuated strain(s). In some embodiments, the composition includes (iii) a H3N2 live attenuated influenza A virus strain, (iv) a B/Victoria/2/87-like live attenuated influenza B virus strain; and (v) a B/Yamagata/16/88-like live attenuated influenza B virus strain.

Where a vaccine of the invention includes two influenza B strains, one B/Victoria/2/87-like strain and one B/Yamagata/16/88-like strain will be included. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [6]. In some embodiments of the invention where two or more influenza B virus strains are present, at least two of the influenza B virus strains may have distinct hemagglutinins but related neuraminidases. For instance, they may both have a B/Victoria/2/87-like neuraminidase [7] or may both have a B/Yamagata/16/88-like neuraminidase. For instance, two B/Victoria/2/87-like encoded neuraminidases may both have one or more of the following sequence characteristics: (1) not a serine at residue 27, but preferably a leucine; (2) not a glutamate at residue 44, but preferably a lysine; (3) not a threonine at residue 46, but preferably an isoleucine; (4) not a proline at residue 51, but preferably a serine; (5) not an arginine at residue 65, but preferably a histidine; (6) not a glycine at residue 70, but preferably a glutamate; (7) not a leucine at residue 73, but preferably a phenylalanine; and/or (8) not a proline at residue 88, but preferably a glutamine. Similarly, in some embodiments the encoded neuraminidase may have a deletion at residue 43, or it may have a threonine; a deletion at residue 43, arising from a trinucleotide deletion in the NA gene, has been reported as a characteristic of B/Victoria/2/87-like strains, although recent strains have regained Thr-43 [7]. Conversely, of course, the opposite characteristics may be shared by two B/Yamagata/16/88-like neuraminidases e.g. S27, E44, T46, P51, R65, G70, L73, and/or P88. These amino acids are numbered relative to the 'Lee40' neuraminidase sequence [8].

Where a vaccine includes more than one strain of influenza, the different strains are typically grown separately and are mixed after the viruses have been harvested and prepared. Thus a process of the invention may include the step of mixing from more than one live attenuated influenza strain. The different strains may be harvested separately, diluted separately, and mixed to give a multivalent live attenuated influenza virus vaccine.

A monovalent live attenuated vaccine of the invention may be administered in conjunction with a trivalent A/H1N1-A/H3N2-B seasonal influenza vaccine, and in particular with a trivalent live attenuated vaccine. The monovalent live attenuated vaccine includes a H1 subtype influenza A virus hemagglutinin which is more closely related to SEQ ID NO: 1 than to SEQ ID NO: 3; the trivalent vaccine includes a H1 subtype influenza A virus hemagglutinin which is more closely related to SEQ ID NO: 3 than to SEQ ID NO: 1. The monovalent live attenuated vaccine may be administered before the trivalent vaccine, after the trivalent vaccine, or at the same time. Where the two vaccines are administered separately, there may be from 2-26 weeks between the administrations.

Reassortants and reverse genetics

The invention can use a reassortant influenza virus strain, and suitable reassortants can be made using reverse genetics. Suitable strains can include at least one other viral gene segment from the AA/6/60 (A/Ann Arbor/6/60) influenza virus strain. Thus the virus may include at least one of segments NP, M, NS, PA, PB1 and/or PB2 from AA/6/60. Viral segments from the AA/6/60 strains, and their sequences, are widely available.

A reassortant virus may include at least one of segments NP, M, NS, PA, PB1 and/or PB2 from AA/6/60. The AA/6/60 strain may be a cold-adapted AA/6/60 strain e.g. its PB1 may include one or more of K391E, E581G &/or A661T mutations in PB1, a N265S mutation in PB2, and/or a D34G mutation in NP [9].

In these reassortant viruses the viral neuraminidase gene may encode a neuraminidase protein which has at least j % sequence identity to SEQ ID NO: 4, where j is 75 or more e.g. 75, 80, 85, 88, 90, 92, 94, 95, 96, 97, 98, 99 or more (e.g. 100). In some embodiments, the neuraminidase is more closely related to SEQ ID NO: 4 than to SEQ ID NO: 5.

The eight segments of the influenza A virus genome encode (i) the PA subunit of the viral polymerase (ii) the PB1 subunit of the viral polymerase (iii) the PB2 subunit of the viral polymerase (iv) the viral nucleoprotein (v) the viral matrix proteins (vi) the viral NS1 and NS2 proteins (vii) hemagglutinin and (viii) neuraminidase. Preferred reassortants of the invention are 6:2 reassortants i.e. they include 6 segments from one strain (e.g. from AA/6/60) but the HA and NA segments from a different strain (e.g. as defined above by reference to SEQ ID NOs 1 and 4). In other embodiments there is a 7:1 reassortant with HA as defined above. In other embodiments the virus includes genes with three different origins, but with at least one segment (e.g. 1, 2, 3, 4, 5, 6) being from AA/6/60.

Reassortant viruses of the invention may have a H1* hemagglutinin with a binding preference for oligosaccharides with a Sia(α2,6)Gal terminal disaccharide compared to oligosaccharides with a Sia(α2,3)Gal terminal disaccharide.

A reassortant virus of the invention may have amino acid proline at residue 200 (numbered according to SEQ ID NO: 1) of its hemagglutinin. For example, it may encode hemagglutinin having sequence SEQ ID NO: 6. Other reassortants may encode hemagglutinin having sequence SEQ ID NO: 7 or SEQ ID NO: 9.

Useful reassortant viruses of the invention can grow in MDCK cells, and the invention provides a method of preparing a virus, comprising steps of: (i) infecting a cell culture with a reassortant virus of the invention; (ii) culturing the cell culture from step (i) to produce further virus; and (iii) purifying virus obtained in step (ii). The method may comprise a further step (iv) processing virus purified in step (iii) to prepare a vaccine, and so the invention provides a method for preparing a vaccine comprising steps (i) to (iv). The vaccine may be a bulk vaccine. It may be used to produce a monovalent final vaccine product or may be used as a component to make a multivalent final vaccine product. The cell culture in step (i) is preferably a MDCK cell culture, but other cells (ideally mammalian cells, such as PER.C6 cells) may be used as an alternative.

The influenza virus may be a reassortant strain obtained by reverse genetics techniques. Reverse genetics techniques [e.g. 10-14] allow influenza viruses with desired genome segments to be prepared in vitro using plasmids, or by plasmid-free systems. Typically, the technique involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [15-17], and these methods will also involve the use of plasmids to express all or some (e.g. just the PB1, PB2, PA and NP proteins) of the viral proteins, with up to 12 plasmids being used in some methods. If canine cells are used, a canine polI promoter may be used [18].

To reduce the number of plasmids needed, one approach [19] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). The method may involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [20]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [21,22].

A live attenuated influenza A virus may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. The inclusion of at least one A/Ann Arbor backbone segment(s) is preferred in live attenuated vaccines. Typically, the invention protects against a strain that is capable of human-to-human transmission, and so the strain's genome will usually include at least one RNA segment that originated in a mammalian (e.g. in a human) influenza virus.

The invention also provides a host cell comprising one or more expression construct(s) for providing the reassortant live attenuated strains described herein. Thus the construct (s) encode a viral hemagglutinin gene with a hemagglutinin which is more closely related to SEQ ID NO: 1 than to SEQ ID NO: 3. The construct(s) will additionally encode the other viral segments for the functional influenza genome, including at least one other viral segment from the AA/6/60 influenza virus strain. The neuraminidase segment may encode a neuraminidase protein which has at least j % sequence identity to SEQ ID NO: 4, etc.

The invention also provides a construct or set of constructs encoding these reassortant strains e.g. when introduced into a host cell. Use of the construct(s) will provide an infectious live attenuated influenza virus in a suitable reverse genetics host system. The constructs may be plasmids or non-plasmid vectors.

The invention also provides a process for RNA expression in a host cell, comprising the use of such construct(s). The invention also provides a method for producing a reassortant live attenuated virus from such construct(s) and/or host cell (s).

The invention also provides a process for preparing a live attenuated influenza vaccine comprising steps of: (i) preparing a reassortant live attenuated influenza virus of the invention by using reverse genetics, wherein the virus has a viral hemagglutinin gene encoding a hemagglutinin which is more closely related to SEQ ID NO: 1 than to SEQ ID NO: 3; (ii) using the reassortant strain to make a vaccine. Step (ii) may involve: culturing a virus (e.g. in eggs or in cell culture); and preparing vaccine from the cultured virus. The cultured virus may be used as an active ingredient in the vaccine.

The invention also provides a process for preparing a live attenuated vaccine comprising a step of using a reassortant influenza virus of the invention which was prepared by using reverse genetics.

Virus growth

The viruses can be grown either on eggs or on cell culture. The current standard method for influenza virus growth uses specific pathogen-free (SPF) embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus.

When cell culture is used, the viral growth substrate will typically be a cell line of mammalian origin. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc.. Preferred mammalian cell lines for growing influenza viruses include: MDCK cells [23-26], derived from Madin Darby canine kidney; Vero cells [27-29], derived from African green monkey (*Cercopithecus aethiops*) kidney; or PER.C6 cells [30], derived from human embryonic retinoblasts. These cell lines are widely available e.g. from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 31-33], including cell lines derived from ducks (e.g. duck retina) or hens. Examples of avian cell lines include avian embryonic stem cells [31,34] and duck retina cells [32]. Suitable avian embryonic stem cells, include the EBx cell line derived from chicken embryonic stem cells, EB45, EB14, and EB14-074 [35]. Chicken embryo fibroblasts (CEF) may also be used.

The most preferred cell lines for growing influenza viruses are MDCK cell lines. The original MDCK cell line is available from the ATCC as CCL-34, but derivatives of this cell line may also be used. For instance, reference 23 discloses a MDCK cell line that was adapted for growth in suspension culture ('MDCK 33016', deposited as DSM ACC 2219). Similarly, reference 36 discloses a MDCK-derived cell line that grows in suspension in serum-free culture ('B-702', deposited as FERM BP-7449). Reference 37 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 38 discloses MDCK cell lines with high susceptibility to infection, including 'MDCK.5F1' cells (ATCC CRL-12042). Any of these MDCK cell lines can be used. MDCK cells are useful for preparing live attenuated vaccines [39, 40].

Where virus has been grown on a mammalian cell line then the composition will advantageously be free from egg proteins (e.g. ovalbumin and ovomucoid) and from chicken DNA, thereby reducing allergenicity.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [41]. Absence of herpes simplex viruses is particularly preferred.

For growth on a cell line, such as on MDCK cells, virus may be grown on cells in suspension [23, 42, 43] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [44] during viral replication e.g. 30-36° C., at 31-35° C., or at 33±1° C.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids may then be stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Virions can be harvested from virus-containing fluids by various methods. For example, a purification process may involve zonal centrifugation using a linear sucrose gradient solution.

A vaccine may be prepared from harvested virus by formulation steps comprising one or more of the following steps: filtration; concentration e.g. by ultracentrifugation; addition of stabilizing buffer; sterile filtration; and/or dilution to a desired potency e.g. to between $10^{6.5}$ and $10^{7.5}$ FFU. When more than one of these formulation steps is used, they are preferably performed in the stated order.

Host cell DNA

Where virus has been grown on a cell line then it is standard practice to minimize the amount of residual cell line DNA in the final vaccine, in order to minimize any oncogenic activity of the DNA. Thus the composition preferably contains less than 10 ng (preferably less than 1 ng, and more preferably less than 100 pg) of residual host cell DNA per dose, although trace amounts of host cell DNA may be present. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay [45,46]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [47]; immunoassay methods, such as the Threshold™ System [48]; and quantitative PCR [49]. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals [48]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 50.

Contaminating DNA can be removed during vaccine preparation using standard purification procedures e.g. chromatography, etc. Removal of residual host cell DNA can be enhanced by nuclease treatment e.g. by using a DNase.

Vaccines containing <10 ng (e.g. <1 ng, <100 pg) host cell DNA per dose are preferred, as are vaccines containing <10 ng (e.g. <1 ng, <100 pg) host cell DNA per dose. Vaccines containing <10 ng (e.g. <1 ng, <100 pg) host cell DNA per dose are more preferred, as are vaccines containing <10 ng (e.g. <1 ng, <100 pg) host cell DNA per dose.

Pharmaceutical compositions

Compositions of the invention are pharmaceutically acceptable. They usually include components in addition to the virus strains e.g. they typically include one or more pharmaceutical carrier(s) and/or excipient(s). A thorough discussion of such components is available in reference 51.

Compositions will generally be in aqueous form.

The composition may include preservatives such as thiomersal (e.g at 10 μg/ml) or 2-phenoxyethanol. It is preferred, however, that the vaccine should be free from mercurial material.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [52], but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The vaccine may include one or more of the following pharmaceutical components e.g. as part of a buffer: monosodium glutamate (e.g. at a final concentration 0.09% w/v, or about 0.19 mg/dose); hydrolyzed porcine gelatin (e.g. at a final concentration 1.00% w/v, or about 2 mg/dose); arginine (e.g. at a final concentration 1.21% w/v, or about 2.4 mg/dose); sucrose (e.g. at a final concentration 6.84% w/v, or about 13.7 mg/dose); and phosphate (e.g. at a final concentration 1.61% w/v).

The pH of a composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The composition is preferably sterile. The composition is preferably gluten free.

Preferred vaccines have a low endotoxin content e.g. less than 1 IU/ml, and preferably less than 0.5 IU/ml. The international unit for endotoxin measurement is well known and can be calculated for a sample by, for instance, comparison to an international standard [53,54], such as the 2nd International Standard (Code 94/580-IS) available from the NIBSC. Current vaccines prepared from virus grown in eggs have endotoxin levels in the region of 0.5-5 IU/ml.

The vaccine may be preferably free from antibiotics (e.g. neomycin, kanamycin, polymyxin B).

The composition may include material for a single immunisation, or may include material for multiple immunisations. Single immunization compositions are more typical.

The vaccine may be prepared for intranasal use and may have a unit dose volume of 0.2 ml dose, which may be administered as 0.1 ml per nostril.

For live vaccines dosing is measured by median tissue culture infectious dose ($TCID_{50}$) or fluorescent focus units (FFU). The vaccine can include a $TCID_{50}$ of between $10^6$ and $10^8$ (preferably between $10^{6.5}$-$10^{7.5}$) per viral strain. The vaccine may have between $10^{6.5}$ and $10^{7.5}$ FFU of each live attenuated virus strain per dose.

Packaging of compositions or kit components

Processes of the invention can include a step in which vaccine is placed into a container, and in particular into a container for distribution for use by physicians.

Suitable containers for the vaccines include vials, nasal sprays, etc., which should be sterile. For intranasal delivery a vaccine can be packaged into a sprayer. The sprayer may be supplied with a tip having a nozzle to produce a mist when activated in the nose.

A composition may be combined (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of treatment, and administration of the vaccine

Compositions of the invention are suitable for administration to human patients, and the invention provides a method of raising an immune response in a patient, comprising the step of administering a composition of the invention to the patient.

The immune response raised by the methods and uses of the invention will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [55]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is intranasal, as in the FLUMIST™ product. A sprayer may produce a mist when activated in the nose. The mist may be deposited primarily in the nose and nasopharynx.

Vaccines prepared according to the invention may be used to treat both children and adults. Influenza vaccines are currently recommended for use in pediatric and adult immunization, from the age of 6 months. Thus the patient may be less than 1 year old (e.g. <6 months old), 1-5 years old, 5-15 years old, 15-55 years old, or at least 55 years old. Preferred patients for receiving the vaccines are the elderly (e.g. ≧50 years old, ≧60 years old, and preferably ≧65 years), the young (e.g. <5 years old, or those aged between 6 months and 24 years, or between 6 months and 4 years, or between 5-18 years), middle aged (25-64 years old), hospitalised patients, healthcare workers, armed service and military personnel, pregnant women, the chronically ill, immunodeficient patients, patients who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population.

Live attenuated vaccines of the invention are particularly useful for subjects who are 2-49 years old.

Some older adults (about a third of those older than 60 years) but few young adults and essentially no children have pre-existing serum antibody against the pandemic A/CA/04/09 strain. Seasonal immunization of young people does not elicit antibodies against this strain [56]. A useful group of subjects to receive compositions of the invention is those subjects who have no existing serum antibody against the pandemic A/CA/04/09 strain e.g. patients born after 1960, after 1970, after 1980, after 1990, or after 2000.

Preferred compositions of the invention satisfy 1, 2 or 3 of the CPMP criteria for efficacy. In adults (18-60 years), these criteria are: (1) ≧70% seroprotection; (2) ≧40% seroconversion; and/or (3) a GMT increase of ≧2.5-fold. In elderly (>60 years), these criteria are: (1) ≧60% seroprotection; (2) ≧30% seroconversion; and/or (3) a GMT increase of ≧2-fold. These criteria are based on open label studies with at least 50 patients. The criteria apply for each strain in a vaccine.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype. Multiple doses will typically be administered at least 1 week apart (e.g. about 2 weeks, about 3 weeks, about 4 weeks, about 6 weeks, about 8 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™). Another antiviral which can be administered is thymosin alpha 1 (e.g. thymalfasin, a 28 amino acid synthetic peptide, available as ZADAXIN™).

Combination vaccines

In addition to the strain and vaccine combinations discussed above, the invention provides a multivalent immunogenic composition comprising (i) a live attenuated influenza A virus with a H1 type hemagglutinin, wherein its hemagglutinin is more closely related to SEQ ID NO: 1 than to SEQ ID NO: 3 and (ii) live attenuated influenza A viruses from 1, 2, 3 or 4 of hemagglutinin subtypes H2, H5, H7 and/or H9. Thus the composition may be H1-H2 bivalent, H1-H7 bivalent, H1-H2-H5 trivalent, H1-H5-H7-H9 tetravalent, H1-H2-H5-H7-H9 pentavalent, etc. At least two strains in the vaccine may share a common neuraminidase subtype e.g. a H1N1-H2N1 bivalent, H1N1-H2N2-H5N1 trivalent, etc.

Mixed-source live attenuated vaccines

Some embodiments of the invention mentioned above are multivalent i.e. they include live attenuated strains for more than one HA type of influenza A virus. The viruses used to prepare a multivalent vaccine may all be grown using the same substrate (e.g. all grown in eggs, or all grown in MDCK culture, etc.) or they may be grown in different substrates (e.g. one strain grown in eggs, another strain grown in cell culture; or one strain grown in MDCK culture or another strain grown in Vero culture).

For example, growth substrates can be chosen according to the growth preferences of a particular strain e.g. if a H1N1 strain grows better in cell culture than in eggs, but an influenza B virus shows the opposite preference, they may be grown on the different substrates and then mixed.

In one embodiment, a live attenuated H1* strain (e.g. H1N1) is grown in cell culture (e.g. in MDCK culture, such as a suspension culture) and another live attenuated strain (e.g. a H3N2 strain, an influenza B strain, etc.) is grown in eggs. Live attenuated viruses are then mixed to provide a multivalent live attenuated influenza vaccine. This process is particularly suitable for preparing a 4-valent live attenuated vaccine with two H1 strains (one a H1* hemagglutinin, one not a H1* hemagglutinin), a H3N2 strain, and one influenza B strain.

Thus the invention provides a live attenuated vaccine comprising at least two different strains of live attenuated influenza virus, wherein a first live attenuated strain is prepared from influenza viruses grown in eggs and a second live attenuated strain is prepared from influenza viruses grown in cell culture. Thus two different strains of live attenuated influenza virus are grown, one in cell culture and one in eggs. Virus is purified from both sources and then mixed to give a vaccine.

The first and second live attenuated strains may both be influenza A virus strains, both influenza B virus strains, or one may be an influenza A virus strain and the other an influenza B virus strain. Preferably at least one of the first and second strains is an influenza A virus strain. Where both the first and second strains is an influenza A virus, these will typically be a H1 and a H3 type strains e.g. from a H1N1 strain and from a H3N2 strain.

Where the first and second strains are influenza A virus strains, one of these can be a H1* strain. It is preferred that the two influenza A strains are not both H1* hemagglutinins, and it is more preferred that the two influenza A strains are not both H1 type. Where a vaccine includes a H1* strain this is preferably the second strain i.e. the H1* strain is grown in cell culture and H1* vaccine strain is then combined with a non-H1* vaccine strain prepared from eggs. In other embodiments, the H1* strain is the first hemagglutinin i.e. the H1* strain is grown in eggs and a H1* strain is then combined with a non-H1* vaccine strain prepared from cell culture.

This mixed-source approach is particularly useful for making a live attenuated vaccine comprising a H1* strain, a non-H1* H1 strain, a H3 strain and an influenza B strain. The H1* strain can be grown in cell culture, and the other three strains (i.e. the usual trivalent mixture for recent seasonal vaccines) can be grown in eggs in the usual manner.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

Identity between polypeptide sequences is preferably determined by the Smith-Waterman homology search algorithm as implemented in the MPSRCH program (Oxford Molecular), using an affine gap search with parameters gap open penalty=12 and gap extension penalty=1.

MODES FOR CARRYING OUT THE INVENTION

Reassortant strain

Mammalian cells were transfected with all 6 backbone segments of influenza A virus strain A/PR/8/34 and the two surface glycoprotein segments from an A/California/04/09 H1N1 strain in a reverse genetics system. An initial assay of culture fluid recovered from the transfected cells showed five positive results for rescued virus (FIG. 1A) and passaging of this material gave many more positive results (FIG. 1B).

To confirm that the observed viruses were true reassortants, strain-specific PCR primers were used to detect the HA, NA and PB1 genes. As shown in FIG. 2, the rescued virus (lanes '1') and the plasmid DNA used in the reverse genetics system (lanes '2') had the same size for all three genes, whereas PCR performed on water (lanes '3') showed no amplification.

Figure 3:
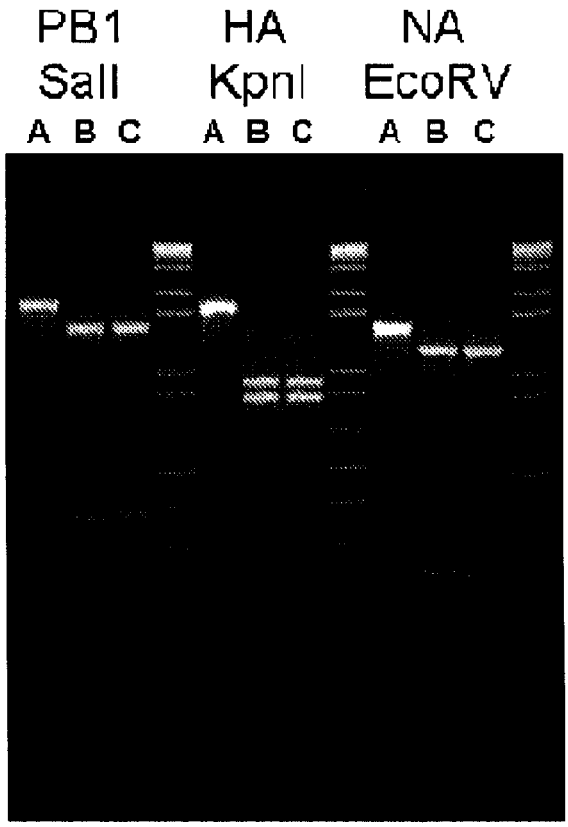
FIG. 3 shows results of a restriction digest.

A restriction digest was then performed on the PCR products. The PB1 gene in PR/8/34 includes a SalI site, whereas the PB1 gene in A/CA/04/09 does not. The HA gene in A/CA/04/09 includes a KpnI site, whereas the HA gene in PR/8/34 does not. The NA gene in A/CA/04/09 includes a EcoRVsite, whereas the NA gene in PR/8/34 does not. Thus these three restriction enzymes can distinguish between the two strains. As shown in FIG. 3 the PCR products (lanes 'A') were digested in all three cases, and the digestion products for the rescued reassortant (lanes 'B') and the original plasmid DNA (lanes 'C') were identical. Thus the virus produced by the reverse genetics system included the HA and NA genes from A/CA/04/09 and PB1 from A/PR/8/34, showing that it has been possible to produce an infectious reassortant virus.

The A/PR/8/34 sequences can easily be replaced by A/AA/6/60 sequences to provide a live attenuated strain suitable for vaccination.

Sequence variations

As discussed above, reverse genetics was used to prepare reassortants of A/CA/04/2009 with a A/PR/8/34 backbone. During this work three different HA sequences were observed: a wild-type sequence, matching the database sequence for A/CA/04/2009 (referred to as F8); a sequence with a Ser200Pro mutation (F9); and a sequence with a Leu208Ile mutation (F10). NB: residue numbering by H3N2 standards is 14 less than given here.

Transfection of either 293T or MDCK cells with plasmid cocktails containing any of the HA variants produced viable reassortant viruses. No infectious virus was recovered from any simultaneous control transfections with plasmid mixtures lacking a HA gene. Growth of the three reassortants (vF8, vF9, and vF10) was compared to the growth of wild type A/CA/04/2009 and A/PR/8/34 in MDCK cells and in embryonated chicken eggs. Virus titer was assayed by formation of infectious foci on MDCK cells (focus formation assay—FFA) and guinea pig red blood cell agglutination (hemagglutination assay—HA). The wild-type A/CA/04/2009 used for these studies was the same virus used to produce the cloned plasmid DNAs, and it had been passaged only once or twice in MDCK cells.

The three reverse genetics reassortants rescued with different HA variants had reproducibly different growth characteristics when grown in MDCK cells and eggs. The F10 variant was significantly less productive by both infectious and HA assays in MDCK cells and in eggs (FIGS. 9-12). The F8 variant grew to approximately 10-fold higher infectious titer and produced more than 4-fold greater HA activity than the other reverse genetics reassortants in MDCK cells (FIGS. 9 & 10), although its performance was comparable to that of the F9 variant in eggs (FIGS. 11 & 12).

To determine if the HA mutations at positions 200 and 208 altered HA antigenicity the hemagglutination inhibition assay (HAI) was assessed with ferret antisera against A/CA/04/2009, A/CA/07/2009, or RG-15 (a reverse genetics-derived A/TX/05/2009-like strain). Databases give identical amino acid sequences from residues 101 to 213 for these three strains. The HAI of all of these antisera with each of the F8-F10 reverse genetics variants were greater than or equivalent to those obtained with A/CA/04/2009, whereas reaction of these variants with normal ferret sera or reaction of A/PR/8/34 virus with these test sera were undetectable. Furthermore, a reverse genetics virus equivalent to F8 with an additional N173D mutation had 8-fold lower HAI titer than A/CA/04. Thus, all of the reverse genetics viruses were antigenically similar to the parental A/CA/04/2009 and A/CA/07/2009 viruses despite the presence of point mutations that improved growth.

Because the variants can increase the growth of reassortants in mammalian cells and eggs, these results demonstrate that sampling viral quasispecies during the rescue of reassortant viruses by reverse genetics can identify useful isolates for vaccine manufacture.

The variable residues at positions 200 and 208 are immediately adjacent to the expected sialic acid binding site. Thus they could affect cell attachment, substrate specificity, growth characteristics, and red blood cell agglutination. These two variations were not reported in two studies that have examined variation in residues near the receptor binding pocket of many H1N1sw isolates [57,58].

It will be understood that the invention has been described by way of example only and modifications may be made whilst remaining within the scope and spirit of the invention.

REFERENCES

[1] Herlocher et al. (2004) J Infect Dis 190(9):1627-30.

[2] Gambaryan & Matrosovich (1992) J Virol Methods 39(1-2):111-23.

[3] Mastrosovich et al. (1999) J Virol 73: 1146-55.

[4] Stevens et al. (2006) J Mol Biol 355:1143-55.

[5] Couceiro & Baum (1994) Mem Inst Oswaldo Cruz 89(4):587-91.

[6] GenBank sequence GI:325176.

[7] McCullers et al. (1999) J Virol 73:7343-8.

[8] GenBank sequence GI:325237.

[9] Jin et al. (2003) Virology 306:18-24.

[10] Hoffmann et al. (2002) Vaccine 20:3165-3170.

[11] Subbarao et al. (2003) Virology 305:192-200.

[12] Liu et al. (2003) Virology 314:580-590.

[13] Ozaki et al. (2004) J. Virol. 78:1851-1857.

[14] Webby et al. (2004) Lancet 363:1099-1103.

[15] WO00/60050.

[16] WO01/04333.

[17] US 6649372.

[18] WO2007/002008.

[19] Neumann et al. (2005) Proc Natl Acad Sci USA 102:16825-9.

[20] WO2006/067211.

[21] WO01/83794.

[22] Hoffmann et al. (2000) Virology 267(2):310-7.

[23] WO97/37000.

[24] Brands et al. (1999) Dev Biol Stand 98:93-100.

[25] Halperin et al. (2002) Vaccine 20:1240-7.

[26] Tree et al. (2001) Vaccine 19:3444-50.

[27] Kistner et al. (1998) Vaccine 16:960-8.

[28] Kistner et al. (1999) Dev Biol Stand 98:101-110.

[29] Bruhl et al. (2000) Vaccine 19:1149-58.

[30] Pau et al. (2001) Vaccine 19:2716-21.

[31] WO03/076601.

[32] WO2005/042728.

[33] WO03/043415.

[34] WO01/85938.

[35] WO2006/108846.

[36] EP-A-1260581 (WO01/64846).

[37] WO2006/071563.

[38] WO2005/113758.

[39] Hussain et al. (2010) Vaccine Comparison of egg and high yielding MDCK cell-derived live attenuated influenza virus for commercial production of trivalent influenza vaccine: In vitro cell susceptibility and influenza virus replication kinetics in permissive and semi-permissive cells.

[40] Yang et al. (2010) Vaccine. 28(19):3308-11.

[41] WO2006/027698.

[42] WO03/023021

[43] WO03/023025

[44] WO97/37001.

[45] Lundblad (2001) Biotechnology and Applied Biochemistry 34:195-197.

[46] Guidance for Industry: Bioanalytical Method Validation. U.S. Department of Health and Human Services Food and Drug Administration Center for Drug Evaluation and Research (CDER) Center for Veterinary Medicine (CVM). May 2001.

[47] Ji et al. (2002) Biotechniques. 32:1162-7.

[48] Briggs (1991) J Parenter Sci Technol. 45:7-12.

[49] Lahijani et al. (1998) Hum Gene Ther. 9:1173-80.

[50] Lokteff et al. (2001) Biologicals. 29:123-32.

[51] Gennaro (2000) Remington: The Science and Practice of Pharmacy. 20th edition, ISBN: 0683306472.

[52] Nony et al. (2001) Vaccine 27:3645-51.

[53] Poole & Mussett (1989) J Biol Stand 17:161-71.

[54] Poole et al. (1997) J. Endotoxin Res 4:221-31

[55] Potter & Oxford (1979) Br Med Bull 35: 69-75.

[56] Centers for Diseases Control and Prevention. (2009) MMWR 58:521.

[57] Garten et al. (2009) Science 325:197-201.

[58] Smith et al. (2009) Nature 459:1122-5.

SEQUENCE LISTING

```
<160> NUMBER OF SEQ ID NOS: 13

<210> SEQ ID NO 1
<211> LENGTH: 566
<212> TYPE: PRT
<213> ORGANISM: Influenza A virus

<400> SEQUENCE: 1

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320
```

-continued

```
Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 2
<211> LENGTH: 326
<212> TYPE: PRT
<213> ORGANISM: Influenza A virus

<400> SEQUENCE: 2

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125
```

-continued

```
Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Thr Tyr Val Phe Val Gly Ser Ser Arg Tyr Ser Lys
        195                 200                 205

Lys Phe Lys Pro Glu Ile Ala Ile Arg Pro Lys Val Arg Asp Gln Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser
                325


<210> SEQ ID NO 3
<211> LENGTH: 566
<212> TYPE: PRT
<213> ORGANISM: Influenza A virus

<400> SEQUENCE: 3

Met Lys Ala Lys Leu Leu Val Leu Leu Cys Ala Leu Ser Ala Thr Asp
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Asn His Asn Gly Lys Leu Cys Lys Leu Lys Gly Ile
    50                  55                  60

Ala Pro Leu Gln Leu Gly Lys Cys Ser Ile Ala Gly Trp Ile Leu Gly
65                  70                  75                  80

Asn Pro Glu Cys Glu Ser Leu Phe Ser Lys Lys Ser Trp Ser Tyr Ile
                85                  90                  95

Ala Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Lys His Asn
    130                 135                 140

Val Thr Lys Gly Val Thr Ala Ala Cys Ser His Lys Gly Lys Ser Ser
145                 150                 155                 160

Phe Tyr Arg Asn Leu Leu Trp Leu Thr Glu Lys Asn Gly Ser Tyr Pro
```

-continued

```
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Glu Asp Gln Lys Thr Ile
        195                 200                 205

Tyr Arg Lys Glu Asn Ala Tyr Val Ser Val Val Ser Ser His Tyr Asn
    210                 215                 220

Arg Arg Phe Thr Pro Glu Ile Ala Lys Arg Pro Lys Val Arg Asn Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Ile Ile
385                 390                 395                 400

Glu Lys Met Asn Thr Gln Phe Thr Ala Val Gly Lys Glu Phe Asn Lys
                405                 410                 415

Leu Glu Lys Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 4

-continued

<211> LENGTH: 469
<212> TYPE: PRT
<213> ORGANISM: Influenza A virus

<400> SEQUENCE: 4

Met Asn Pro Asn Gln Lys Ile Ile Thr Ile Gly Ser Val Cys Met Thr
1 5 10 15

Ile Gly Met Ala Asn Leu Ile Leu Gln Ile Gly Asn Ile Ile Ser Ile
20 25 30

Trp Ile Ser His Ser Ile Gln Leu Gly Asn Gln Asn Gln Ile Glu Thr
35 40 45

Cys Asn Gln Ser Val Ile Thr Tyr Glu Asn Asn Thr Trp Val Asn Gln
50 55 60

Thr Tyr Val Asn Ile Ser Asn Thr Asn Phe Ala Ala Gly Gln Ser Val
65 70 75 80

Val Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Asn Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Val Met Thr Asp Gly Pro Ser Asn Gly Gln Ala Ser Tyr Lys Ile Phe
245 250 255

Arg Ile Glu Lys Gly Lys Ile Val Lys Ser Val Glu Met Asn Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Ile Gly Tyr Ile Cys Ser Gly
305 310 315 320

Ile Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Ile Ser Ser Arg
355 360 365

Asn Gly Phe Glu Met Ile Trp Asp Pro Asn Gly Trp Thr Gly Thr Asp
370 375 380

Asn Asn Phe Ser Ile Lys Gln Asp Ile Val Gly Ile Asn Glu Trp Ser

-continued

```
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 5
<211> LENGTH: 470
<212> TYPE: PRT
<213> ORGANISM: Influenza A virus

<400> SEQUENCE: 5

Met Asn Pro Asn Gln Lys Ile Ile Thr Ile Gly Ser Ile Cys Met Thr
 1               5                  10                  15

Ile Gly Ile Ile Ser Leu Ile Leu Gln Ile Gly Asn Ile Ile Ser Ile
            20                  25                  30

Trp Val Ser His Ser Ile Gln Thr Gly Ser Gln Asn His Thr Gly Ile
        35                  40                  45

Cys Asn Gln Arg Ile Ile Thr Tyr Glu Asn Ser Thr Trp Val Asn Gln
    50                  55                  60

Thr Tyr Val Asn Ile Asn Asn Thr Asn Val Val Ala Gly Lys Asp Thr
65                  70                  75                  80

Thr Ser Val Thr Leu Ala Gly Asn Ser Ser Leu Cys Pro Ile Arg Gly
                85                  90                  95

Trp Ala Ile Tyr Ser Lys Asp Asn Ser Ile Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Ala Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asp Gly Ala Val Ala Val Leu Lys Tyr
        195                 200                 205

Asn Gly Ile Ile Thr Glu Thr Ile Lys Ser Trp Arg Lys Arg Ile Leu
    210                 215                 220

Arg Thr Gln Glu Ser Glu Cys Val Cys Val Asn Gly Ser Cys Phe Thr
225                 230                 235                 240

Ile Met Thr Asp Gly Pro Ser Asn Gly Pro Ala Ser Tyr Arg Ile Phe
                245                 250                 255

Lys Ile Glu Lys Gly Lys Ile Thr Lys Ser Ile Glu Leu Asp Ala Pro
            260                 265                 270

Asn Ser His Tyr Glu Glu Cys Ser Cys Tyr Pro Asp Thr Gly Thr Val
        275                 280                 285
```

-continued

```
Met Cys Val Cys Arg Asp Asn Trp His Gly Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Pro Lys Asp Gly Lys Gly Ser Cys Asp
                325                 330                 335

Pro Val Thr Val Asp Gly Ala Asp Gly Val Lys Gly Phe Ser Tyr Arg
            340                 345                 350

Tyr Gly Asn Gly Val Trp Ile Gly Arg Thr Lys Ser Asn Ser Ser Arg
        355                 360                 365

Lys Gly Phe Glu Met Ile Trp Asp Pro Asn Gly Trp Thr Asp Thr Asp
    370                 375                 380

Ser Asn Phe Leu Val Lys Gln Asp Val Val Ala Met Thr Asp Trp Ser
385                 390                 395                 400

Gly Tyr Ser Gly Ser Phe Val Gln His Pro Glu Leu Thr Gly Leu Asp
                405                 410                 415

Cys Met Arg Pro Cys Phe Trp Val Glu Leu Val Arg Gly Arg Pro Arg
            420                 425                 430

Glu Gly Thr Thr Val Trp Thr Ser Gly Ser Ser Ile Ser Phe Cys Gly
        435                 440                 445

Val Asn Ser Asp Thr Ala Asn Trp Ser Trp Pro Asp Gly Ala Glu Leu
    450                 455                 460

Pro Phe Thr Ile Asp Lys
465                 470


<210> SEQ ID NO 6
<211> LENGTH: 566
<212> TYPE: PRT
<213> ORGANISM: Influenza A virus

<400> SEQUENCE: 6

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190
```

-continued

```
Leu Trp Gly Ile His His Pro Pro Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 7
<211> LENGTH: 565
<212> TYPE: PRT
<213> ORGANISM: Influenza A virus -continued

<400> SEQUENCE: 7

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Gly Val Thr Ala Ala Cys Pro His Ala Gly Ala Lys Ser Phe
145 150 155 160

Tyr Lys Asn Leu Ile Trp Leu Val Lys Lys Gly Asn Ser Tyr Pro Lys
165 170 175

Leu Ser Lys Ser Tyr Ile Asn Asp Lys Gly Lys Glu Val Leu Val Leu
180 185 190

Trp Gly Ile His His Pro Ser Thr Ser Ala Glu Gln Gln Ser Leu Tyr
195 200 205

Gln Asn Ala Asp Thr Tyr Val Phe Val Gly Ser Ser Arg Tyr Ser Lys
210 215 220

Lys Phe Lys Pro Glu Ile Ala Ile Arg Pro Lys Val Arg Asp Gln Glu
225 230 235 240

Gly Arg Met Asn Tyr Tyr Trp Thr Leu Val Glu Pro Gly Asp Lys Ile
245 250 255

Thr Phe Glu Ala Thr Gly Asn Leu Val Val Pro Arg Tyr Ala Phe Ala
260 265 270

Met Glu Arg Asn Ala Gly Ser Gly Ile Ile Ile Ser Asp Thr Pro Val
275 280 285

His Asp Cys Asn Thr Thr Cys Gln Thr Pro Lys Gly Ala Ile Asn Thr
290 295 300

Ser Leu Pro Phe Gln Asn Ile His Pro Ile Thr Ile Gly Lys Cys Pro
305 310 315 320

Lys Tyr Val Lys Ser Thr Lys Leu Arg Leu Ala Thr Gly Leu Arg Asn
325 330 335

Ile Pro Ser Ile Gln Ser Arg Gly Leu Phe Gly Ala Ile Ala Gly Phe
340 345 350

Ile Glu Gly Gly Trp Thr Gly Met Val Asp Gly Trp Tyr Gly Tyr His
355 360 365

His Gln Asn Glu Gln Gly Ser Gly Tyr Ala Ala Asp Leu Lys Ser Thr
370 375 380

Gln Asn Ala Ile Asp Glu Ile Thr Asn Lys Val Asn Ser Val Ile Glu
385 390 395 400

Lys Met Asn Thr Gln Phe Thr Ala Val Gly Lys Glu Phe Asn His Leu
405 410 415

-continued

```
Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 8
<211> LENGTH: 325
<212> TYPE: PRT
<213> ORGANISM: Influenza A virus

<400> SEQUENCE: 8

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Gly Val Thr Ala Ala Cys Pro His Ala Gly Ala Lys Ser Phe Tyr
    130                 135                 140

Lys Asn Leu Ile Trp Leu Val Lys Lys Gly Asn Ser Tyr Pro Lys Leu
145                 150                 155                 160

Ser Lys Ser Tyr Ile Asn Asp Lys Gly Lys Glu Val Leu Val Leu Trp
                165                 170                 175

Gly Ile His His Pro Ser Thr Ser Ala Glu Gln Gln Ser Leu Tyr Gln
            180                 185                 190

Asn Ala Asp Thr Tyr Val Phe Val Gly Ser Ser Arg Tyr Ser Lys Lys
        195                 200                 205

Phe Lys Pro Glu Ile Ala Ile Arg Pro Lys Val Arg Asp Gln Glu Gly
```

-continued

```
    210                 215                 220

Arg Met Asn Tyr Tyr Trp Thr Leu Val Glu Pro Gly Asp Lys Ile Thr
225                 230                 235                 240

Phe Glu Ala Thr Gly Asn Leu Val Val Pro Arg Tyr Ala Phe Ala Met
                245                 250                 255

Glu Arg Asn Ala Gly Ser Gly Ile Ile Ile Ser Asp Thr Pro Val His
            260                 265                 270

Asp Cys Asn Thr Thr Cys Gln Thr Pro Lys Gly Ala Ile Asn Thr Ser
        275                 280                 285

Leu Pro Phe Gln Asn Ile His Pro Ile Thr Ile Gly Lys Cys Pro Lys
    290                 295                 300

Tyr Val Lys Ser Thr Lys Leu Arg Leu Ala Thr Gly Leu Arg Asn Ile
305                 310                 315                 320

Pro Ser Ile Gln Ser
                325


<210> SEQ ID NO 9
<211> LENGTH: 565
<212> TYPE: PRT
<213> ORGANISM: Influenza A virus

<400> SEQUENCE: 9

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Gly Val Thr Ala Ala Cys Pro His Ala Gly Ala Ser Ser Phe
145                 150                 155                 160

Tyr Lys Asn Leu Ile Trp Leu Val Glu Lys Gly Asn Ser Tyr Pro Lys
                165                 170                 175

Leu Ser Lys Ser Tyr Ile Asn Asp Lys Gly Lys Glu Val Leu Val Leu
            180                 185                 190

Trp Gly Ile His His Pro Ser Thr Ser Ala Glu Gln Ser Ser Leu Tyr
        195                 200                 205

Gln Asn Ala Asp Thr Tyr Val Phe Val Gly Ser Ser Arg Tyr Ser Lys
    210                 215                 220

Lys Phe Lys Pro Glu Ile Ala Ile Arg Pro Lys Val Arg Asp Gln Ala
225                 230                 235                 240

Gly Arg Met Asn Tyr Tyr Trp Thr Leu Val Glu Pro Gly Asp Lys Ile
                245                 250                 255
```

-continued

```
Thr Phe Glu Ala Thr Gly Asn Leu Val Val Pro Arg Tyr Ala Phe Ala
            260                 265                 270

Met Glu Arg Asn Ala Gly Ser Gly Ile Ile Ile Ser Asp Thr Pro Val
        275                 280                 285

His Asp Cys Asn Thr Thr Cys Gln Thr Pro Lys Gly Ala Ile Asn Thr
    290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565


<210> SEQ ID NO 10
<211> LENGTH: 325
<212> TYPE: PRT
<213> ORGANISM: Influenza A virus

<400> SEQUENCE: 10

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60
```

```
Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Gly Val Thr Ala Ala Cys Pro His Ala Gly Ala Ser Ser Phe Tyr
    130                 135                 140

Lys Asn Leu Ile Trp Leu Val Glu Lys Gly Asn Ser Tyr Pro Lys Leu
145                 150                 155                 160

Ser Lys Ser Tyr Ile Asn Asp Lys Gly Lys Glu Val Leu Val Leu Trp
                165                 170                 175

Gly Ile His His Pro Ser Thr Ser Ala Glu Gln Ser Ser Leu Tyr Gln
            180                 185                 190

Asn Ala Asp Thr Tyr Val Phe Val Gly Ser Ser Arg Tyr Ser Lys Lys
        195                 200                 205

Phe Lys Pro Glu Ile Ala Ile Arg Pro Lys Val Arg Asp Gln Ala Gly
    210                 215                 220

Arg Met Asn Tyr Tyr Trp Thr Leu Val Glu Pro Gly Asp Lys Ile Thr
225                 230                 235                 240

Phe Glu Ala Thr Gly Asn Leu Val Val Pro Arg Tyr Ala Phe Ala Met
                245                 250                 255

Glu Arg Asn Ala Gly Ser Gly Ile Ile Ile Ser Asp Thr Pro Val His
            260                 265                 270

Asp Cys Asn Thr Thr Cys Gln Thr Pro Lys Gly Ala Ile Asn Thr Ser
        275                 280                 285

Leu Pro Phe Gln Asn Ile His Pro Ile Thr Ile Gly Lys Cys Pro Lys
    290                 295                 300

Tyr Val Lys Ser Thr Lys Leu Arg Leu Ala Thr Gly Leu Arg Asn Ile
305                 310                 315                 320

Pro Ser Ile Gln Ser
                325


<210> SEQ ID NO 11
<211> LENGTH: 566
<212> TYPE: PRT
<213> ORGANISM: Influenza A virus

<400> SEQUENCE: 11

Met Lys Ala Ile Leu Val Val Leu Leu Tyr Thr Phe Ala Thr Ala Asn
 1               5                  10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
```

-continued

```
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220

Lys Thr Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525
```

```
Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565


<210> SEQ ID NO 12
<211> LENGTH: 326
<212> TYPE: PRT
<213> ORGANISM: Influenza A virus

<400> SEQUENCE: 12

Asp Thr Leu Cys Ile Gly Tyr His Ala Asn Asn Ser Thr Asp Thr Val
 1               5                  10                  15

Asp Thr Val Leu Glu Lys Asn Val Thr Val Thr His Ser Val Asn Leu
            20                  25                  30

Leu Glu Asp Lys His Asn Gly Lys Leu Cys Lys Leu Arg Gly Val Ala
        35                  40                  45

Pro Leu His Leu Gly Lys Cys Asn Ile Ala Gly Trp Ile Leu Gly Asn
    50                  55                  60

Pro Glu Cys Glu Ser Leu Ser Thr Ala Ser Ser Trp Ser Tyr Ile Val
65                  70                  75                  80

Glu Thr Pro Ser Ser Asp Asn Gly Thr Cys Tyr Pro Gly Asp Phe Ile
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Thr Ser Ser Trp Pro Asn His Asp Ser
        115                 120                 125

Asn Lys Gly Val Thr Ala Ala Cys Pro His Ala Gly Ala Lys Ser Phe
    130                 135                 140

Tyr Lys Asn Leu Ile Trp Leu Val Lys Lys Gly Asn Ser Tyr Pro Lys
145                 150                 155                 160

Leu Ser Lys Ser Tyr Ile Asn Asp Lys Gly Lys Glu Val Leu Val Leu
                165                 170                 175

Trp Gly Ile His His Pro Ser Thr Ser Ala Asp Gln Gln Ser Leu Tyr
            180                 185                 190

Gln Asn Ala Asp Ala Tyr Val Phe Val Gly Ser Ser Arg Tyr Ser Lys
        195                 200                 205

Thr Phe Lys Pro Glu Ile Ala Ile Arg Pro Lys Val Arg Asp Arg Glu
    210                 215                 220

Gly Arg Met Asn Tyr Tyr Trp Thr Leu Val Glu Pro Gly Asp Lys Ile
225                 230                 235                 240

Thr Phe Glu Ala Thr Gly Asn Leu Val Val Pro Arg Tyr Ala Phe Ala
                245                 250                 255

Met Glu Arg Asn Ala Gly Ser Gly Ile Ile Ile Ser Asp Thr Pro Val
            260                 265                 270

His Asp Cys Asn Thr Thr Cys Gln Thr Pro Lys Gly Ala Ile Asn Thr
        275                 280                 285

Ser Leu Pro Phe Gln Asn Ile His Pro Ile Thr Ile Gly Lys Cys Pro
    290                 295                 300

Lys Tyr Val Lys Ser Thr Lys Leu Arg Leu Ala Thr Gly Leu Arg Asn
305                 310                 315                 320

Ile Pro Ser Ile Gln Ser
```

325

<210> SEQ ID NO 13
<211> LENGTH: 566
<212> TYPE: PRT
<213> ORGANISM: Influenza A virus

<400> SEQUENCE: 13

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

Asn Pro Glu Cys Glu Ser Leu Ser Thr Ala Ser Ser Trp Ser Tyr Ile
85 90 95

Val Glu Thr Pro Ser Ser Asp Asn Gly Thr Cys Tyr Pro Gly Asp Phe
100 105 110

Ile Asp Tyr Glu Glu Leu Arg Glu Gln Leu Ser Ser Val Ser Ser Phe
115 120 125

Glu Arg Phe Glu Ile Phe Pro Lys Thr Ser Ser Trp Pro Asn His Asp
130 135 140

Ser Asn Lys Gly Val Thr Ala Ala Cys Pro His Ala Gly Ala Lys Ser
145 150 155 160

Phe Tyr Lys Asn Leu Ile Trp Leu Val Lys Lys Gly Asn Ser Tyr Pro
165 170 175

Lys Leu Ser Lys Ser Tyr Ile Asn Asp Lys Gly Lys Glu Val Leu Val
180 185 190

Leu Trp Gly Ile His His Pro Ser Thr Ser Ala Asp Gln Gln Ser Ile
195 200 205

Tyr Gln Asn Ala Asp Thr Tyr Val Phe Val Gly Ser Ser Arg Tyr Ser
210 215 220

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr
355 360 365

-continued

```
His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

The invention claimed is:

1. An influenza A virus, wherein (a) the viral hemagglutinin gene encodes a hemagglutinin which is more closely related to SEQ ID NO: 1 than to SEQ ID NO: 3 and (b) at least one other viral gene is from the AA/6/60 influenza A virus strain.

2. An influenza A virus, wherein (a) the viral hemagglutinin gene encodes a hemagglutinin protein which has at least 90% sequence identity to SEQ ID NO: 1, and (b) at least one other viral gene is from the AA/6/60 influenza A virus strain.

* * * * *